United States Patent [19]

Hutchison et al.

[11] Patent Number: 5,440,131
[45] Date of Patent: Aug. 8, 1995

[54] WIPER ASSEMBLY FOR ULTRAVIOLET-LIGHT REACTOR TUBES

[75] Inventors: Joseph A. Hutchison, Dallas; Paul T. Schertz, Carrollton, both of Tex.

[73] Assignee: Solar Kinetics Inc., Dallas, Tex.

[21] Appl. No.: 278,407

[22] Filed: Jul. 21, 1994

[51] Int. Cl.6 .................................. A61L 2/10
[52] U.S. Cl. .................. 250/435; 250/436; 250/455.11; 422/24
[58] Field of Search .............. 250/431, 435, 455.11, 250/436, 432 R, 428, 504 R; 422/24

[56] References Cited

U.S. PATENT DOCUMENTS

| | | | |
|---|---|---|---|
| 4,367,410 | 1/1983 | Wood | 250/431 |
| 4,766,321 | 8/1988 | Lew et al. | 250/431 |
| 4,922,114 | 5/1990 | Boehme | 250/435 |

Primary Examiner—Jack I. Berman
Assistant Examiner—James Beyer
Attorney, Agent, or Firm—Crutsinger & Booth

[57] ABSTRACT

A wiper assembly is provided for cleaning the reactor tubes of an ultraviolet-light reactor. The wiper assembly is positioned inside a reactor chamber of the ultraviolet-light reactor. The wiper assembly includes a wiper that has a circular opening sufficiently large to accommodate a reactor tube. A wiper blade is formed on the wiper circumferential of the opening and being deflected such that when the reactor tube is positioned through the opening, the blade engages the outer surface of the reactor tube. The wiper is formed of a plastic material. The wiper is connected to a platform positioned within the reactor chamber. The platform supports the wiper in the reactor chamber such that the reactor tube extends through the opening in the wiper. According to one aspect of the invention, at least one rod is connected to the platform. The rod extends out of the reactor chamber. The rod can be moved from outside the reactor chamber for mechanically reciprocating the platform along the length of the reactor tube in the chamber, whereby, the wiper blade slides along the outer surface of the reactor tube to wipe off at least some of the fouling that may have accumulated on the outer surface of the reactor tube. According to another aspect of the invention, the platform is supported by a plurality of floats to move with the fluid level in the reactor chamber.

7 Claims, 3 Drawing Sheets

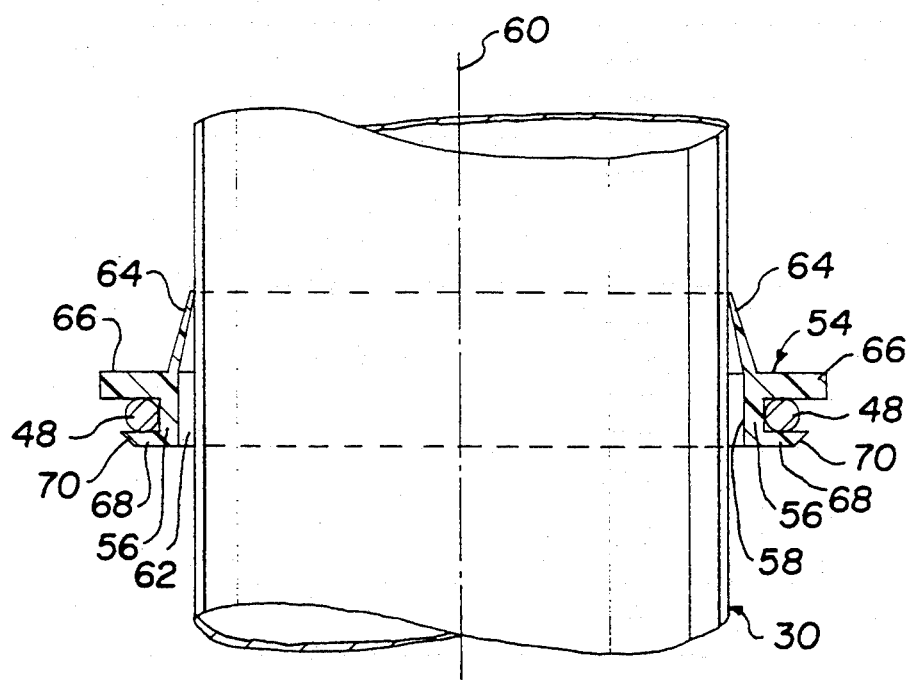
Figure 3
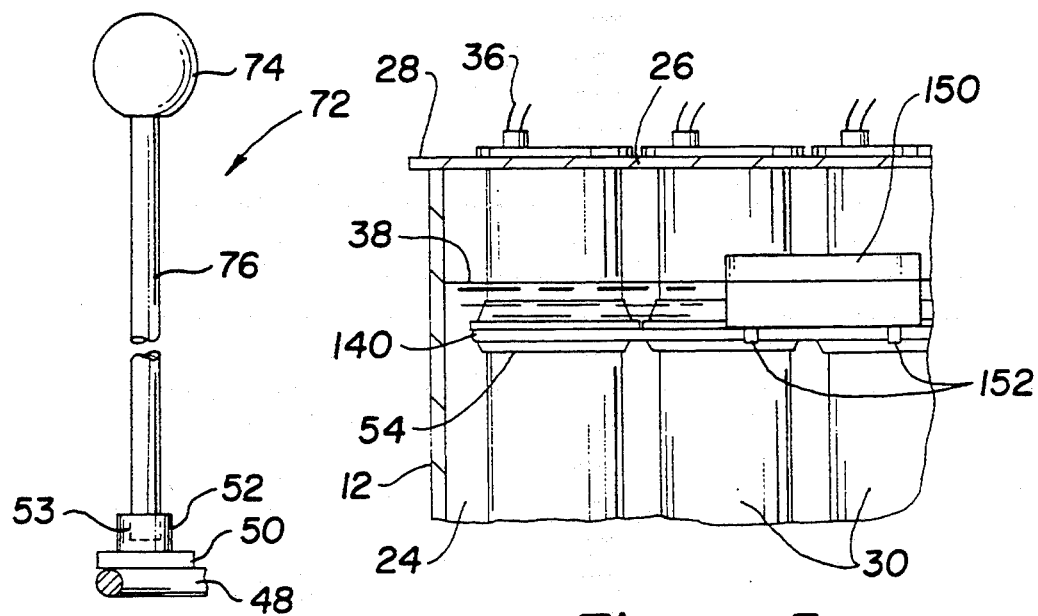
Figure 4
Figure 5

WIPER ASSEMBLY FOR ULTRAVIOLET-LIGHT REACTOR TUBES

TECHNICAL FIELD

This invention relates to a wiper assembly for removing fouling and scale build up from a reactor tube in an ultraviolet-light reactor.

BACKGROUND OF THE INVENTION

Ultraviolet light is a portion of the electromagnetic spectrum that has many uses. For example, ultraviolet light can be used in a purification system to kill bacteria and break down chemicals in a fluid, such as water or air. The ultraviolet radiation can converts chemicals in the water to carbon dioxide and water. If halogenated compounds are present, the ultraviolet radiation converts them into halogenated acids. Ultraviolet light can also be used in photosynthetic reactions to initiate and cause chemical reactions to make chemical compounds. These ultraviolet-light initiated reactions can take place in a gas or liquid phase. To be effective, the fluid must be exposed to ultraviolet-light radiation of a certain minimum intensity for a certain minimum time. The minimum intensity and time required for a particular process is determined by routine experimentation and analysis. Generally, the more intense the ultraviolet-light radiation, the shorter the exposure time required for a given purification or reaction objective.

As is well known in the art, an ultraviolet lamp is typically made with a straight, hollow tube of UV transparent material, typically quartz. The straight tube is sealed at both ends such that electrical connections extend through the seals into the tube. The tube is filled with a gas that is known to produce ultraviolet light when a sufficient electrical current passes through the gas.

To immerse an ultraviolet lamp in water, at least one end of the straight-tube lamp and its electrical connections are normally positioned below the surface level of the water. To protect the electrical connections of the lamp, it is normally positioned in a secondary sheath of ultraviolet transparent material. A suitable ultraviolet transparent material for the sheath is quartz, which is transparent to both ultraviolet and visible light and has some physical properties similar to glass. The quartz sheath of the reactor tube keeps water away from the lamp and its electrical connections. The ultraviolet lamp with its protective sheath is referred to herein as a reactor tube.

An ultraviolet-light reactor typically includes a tank or other chamber for holding or circulating a fluid to be treated with ultraviolet radiation. An ultraviolet reactor tube comprising the lamp and its protective quartz sheath is positioned in the reactor chamber so that fluid in the chamber is exposed to the ultraviolet radiation. Some ultraviolet-light reactors have a plurality of reactor tubes positioned in the chamber, which can provide intense ultraviolet radiation. Since the ultraviolet-light generating efficiency of a lamp gradually deteriorates with use, another purpose of the protective sheath is to allow a lamp to be periodically changed without opening the reactor chamber. In an ultraviolet-light reactor having a plurality of reactor tubes, the lamp of one reactor tube can be changed without interrupting the ultraviolet-light treatment provided by the other reactor tubes.

A problem with ultraviolet reactor tubes is that they tend to become fouled and accumulate scale. This problem is particularly acute in water treatment reactors. As fouling and scale accumulates on the outer surface of the reactor tube, it increasingly blocks the ultraviolet light from the lamp, which reduces the intensity and effectiveness of the ultraviolet-light treatment. To remove the fouling and scale, the protective sheath of the reactor tube has to be mechanically or chemically cleaned. Furthermore, the reactor tubes are often positioned in an ultraviolet-light reactor such that they are inaccessible for cleaning without at least partially dismantling the reactor. This is particularly so with a reactor that uses a plurality of reactor tubes in a chamber. For example, an ultraviolet-light reactor can have thirty reactor tubes in a single chamber. The necessary cleaning of the reactor tube to maintain the performance of the reactor has been time consuming and expensive. Thus, there has been a long-felt need for apparatus and method for cleaning the reactor tubes of an ultraviolet-light reactor.

SUMMARY OF THE INVENTION

Apparatus and methods are provided for cleaning accumulated fouling on one or more reactor tubes in an ultraviolet-light reactor chamber.

An ultraviolet-light reactor is provided. The reactor is particularly adapted for water treatment, however, variations in the illustrated design can be made for the treatment of other fluids or for performing photosynthetic chemical reactions. The ultraviolet-light reactor has a fluid treatment chamber. The reactor includes at least one reactor tube, but more preferably a plurality of reactor tubes positioned in parallel in the treatment chamber. The chamber has one or more ports for filling and draining the reactor with a fluid to be treated with ultraviolet radiation. In another embodiment of the invention, the reactor can be operated continuously, with fluid flowing in through one port, circulating in the reactor, and then flowing out another port, such that it circulates for a desired minimum "residence time" in the reactor chamber. The fluid can flow under natural pressure or it can be mechanically pumped through the reactor.

To solve the problem of fouling of the reactor tube, a wiper assembly is provided. The wiper assembly is positioned inside the chamber of the ultraviolet-light reactor. The wiper assembly includes a platform for supporting a wiper. The wiper has an opening that is similar in shape to the cross section of the reactor tube but larger, thus, there is at least a sufficient clearance defined between the wiper opening and the reactor tube that allows the wiper to move freely up and down along the length of the reactor tube. The wiper opening has a peripheral blade that is deflected such that the blade can engage the surface of a reactor tube positioned through the wiper opening. When the wiper is moved by the platform along the length of the reactor tube, the blade slides along the outer surface of the reactor tube, thereby wiping or scraping off any fouling that may have accumulated on the tube.

The reactor tube wiper is preferably integrally formed of a resilient material such as a plastic. Most preferably, the wiper is formed of a plastic material that is resistant to ultraviolet light degradation, such as polytetrafluoroethylene (PTFE), which is commercially available under the trademark "TEFLON". The wiper is also preferably adapted to be removably connected to an opening in the platform, such that a worn wiper can be replaced with a new wiper.

The wiper assembly has at least one means for moving the platform along the length of the reactor tube in the reactor chamber. For example, the wiper assembly can have a slide rod for moving the platform. The slide rod can be moved from outside the reactor for reciprocating the platform inside the reactor chamber. In the process of reciprocally moving the wiper assembly along the length of the reactor tube, the wiper cleans fouling from the reactor tube surface. Wiping the reactor tube is usually more effective if there is a liquid, such as water, in the reactor chamber. If desired, the removed fouling can be flushed from the chamber with a purge flow cycle. Cleaning of the reactor tube can be accomplished without dismantling the reactor.

According to another embodiment of the invention, the wiper assembly can be provided with one or more floats whereby the wiper assembly floats near the surface of the water in the reactor chamber. Thus, the wiper assembly lowers with the water level when the reactor chamber is drained, and raises when the chamber is filled. With each lowering or raising of the wiper assembly, the wiper cleans fouling from the reactor tube surface. In batch treatment processes, the reactor tubes are cleaned with each batch of water to be treated with the filling and draining of the reactor chamber. Otherwise, the reactor chamber can be periodically drained and filled for the purpose of lowering and raising the floating wiper assembly. The floats can be used in combination with slide rods for moving the wiper assembly independently of the water level.

These and other features, advantages, and objects of the present invention will be apparent to those skilled in the art upon reading the following detailed description of preferred embodiments and referring to the drawings.

BRIEF DESCRIPTION OF THE DRAWINGS

The accompanying drawings are incorporated into and form a part of the specification to illustrate several examples of the present invention. These drawings together with the description serve to explain the principles of the invention. The drawings are only for the purpose of illustrating preferred and alternative examples of how the invention can be made and used and are not to be construed as limiting the invention to only the illustrated and described examples. The various advantages and features of the present invention will be apparent from a consideration of the drawings in which:

FIG. 3 is a side elevation detail of one of the wipers of the wiper assembly;

FIG. 4 illustrates the lift rod for manually raising and lowering the wiper assembly to clean the outer surfaces of the reactor tubes; and FIG. 5 illustrates an alternative preferred embodiment of the invention in which the wiper assembly is supported by one or more floats to move with the water level in the reactor chamber.

DETAILED DESCRIPTION OF PREFERRED EMBODIMENTS

Figure 1:
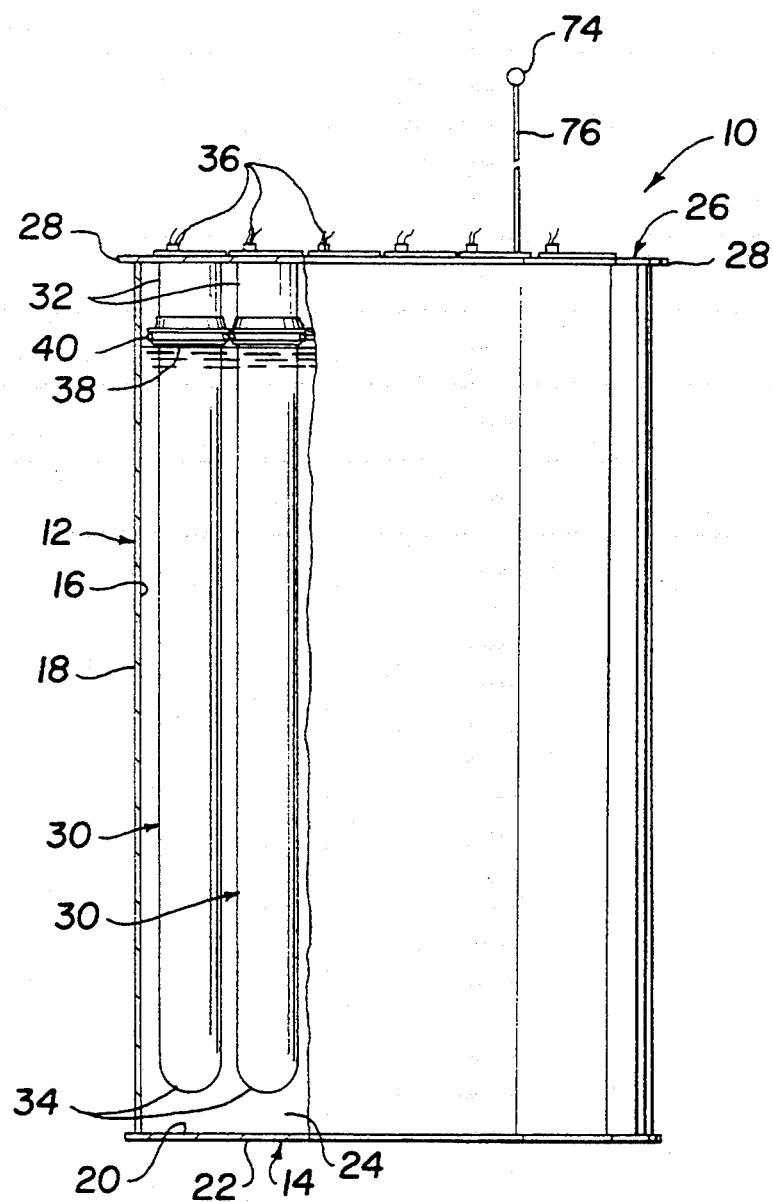
FIG. 1 is a partial cross-sectional illustration of an ultraviolet-light reactor for treating a fluid, such as water, according to a preferred embodiment of the invention, in which a plurality of quartz reactor tubes for protectively containing ultraviolet lamps are positioned in a reactor chamber that has a wiper assembly mounted in the chamber to reciprocally slide along the length of the reactor tubes.

The present invention will be described by referring to apparatuses and methods showing various examples of how the invention can be made and used. Like reference characters are used throughout the several views of the drawing to indicate like or corresponding parts.

Referring to FIG. 1 of the drawings, the reference numeral 10 generally refers to an ultraviolet-light reactor according to a presently most preferred embodiment of the invention. The illustrated ultraviolet-light reactor 10 is particularly adapted for water purification. It is to be understood, however, that variations in the illustrated design can be made for the treatment of other fluids or for performing photosynthetic chemical reactions.

The ultraviolet-light reactor 10 has a cylindrical side wall 12 and a circular bottom wall 14. It is to be understood, however, that the reactor 10 can have any suitable shape and need not be cylindrical but could have a rectangular or other shape. The side wall 12 has an inner surface 16 and an outer surface 18. Similarly, the bottom wall 14 has an inner surface 20 and an outer surface 22. In the illustrated embodiment, the side wall 12 and bottom wall 14 are formed of a suitable watertight structural material, such as stainless steel. The side wall 12 and bottom wall 14 are welded or otherwise joined to define a watertight reactor chamber 24. The reactor 10 also has a top wall 26. Top wall 26 can be, but need not be watertight. Top wall 26 can be removably supported on the side wall 12 by the circumferentially extending lip portion 28. In a preferred embodiment of the invention, the inner surface 20 of side wall 12 and the inner surface 20 of bottom wall 14 are at least partially reflective to ultraviolet radiation.

The ultraviolet-light reactor 10 includes a plurality of reactor tubes, such as illustrated tubes 30. The sheath of each reactor tube 30 is typically cylindrical in shape having a circular cross-section and an axial length, with an upper, open end 32 and a lower, closed end 34. The top wall 26 has a plurality of openings (not shown) formed therein for supporting the upper, open end 32 of each of the quartz sheaths. An ultraviolet lamp (not shown) is inserted into the quartz sheath through upper, open end 32 and positioned in the sheath. The electrical connections 36 of an ultraviolet lamp can extend above the upper end 32 of the reactor tube 30. The sheath of each reactor tube 30 is preferably formed of quartz, which is highly transparent to ultraviolet light and has good physical properties. For example, quartz can be formed into a glass-like substance that is watertight. Quartz is transparent to visible light, so the condition of the ultraviolet lamps therein can be visually inspected for breakage. (Ultraviolet light can be damaging to the eyes, however, so the lamps should not be looked at during operation without suitable ultraviolet protective goggles.) Quartz also has good structural properties for protecting an ultraviolet lamp positioned in the sheath.

As shown in FIG. 1, the chamber 24 of the reactor 10 can be filled with water to a desired water level, such as level 38. For this purpose, there can be one or more ports (not shown) in the side wall 12 for filling and draining the reactor. The water in the reactor chamber 24 can be treated for an effective amount of time to break down pollutant chemicals and kill bacteria. The amount of time required will depend on several factors, such as the intensity of ultraviolet-light radiation produced by the reactor tubes 30, the chemical reactions desired, etc., but can be determined by known analytical techniques. After the ultraviolet-light treatment is sufficiently complete, the water can be drained from the reactor and subsequently refilled with another amount of water to be treated. In another preferred embodiment of the invention, the reactor 10 can be operated continuously, with water flowing in through one port, circulating in the reactor chamber, and then flowing out of another port. The water is circulated through the reactor chamber at a slow enough rate so that it has a desired "residence time" in the reactor 10.

To solve the problem of fouling of the reactor tubes 30, a wiper assembly, which is generally referred to by the reference numeral 40, is positioned inside the reactor 10. The wiper assembly 40 will be described in more detail with reference to FIGS. 2-4 of the drawings.

Figure 2:
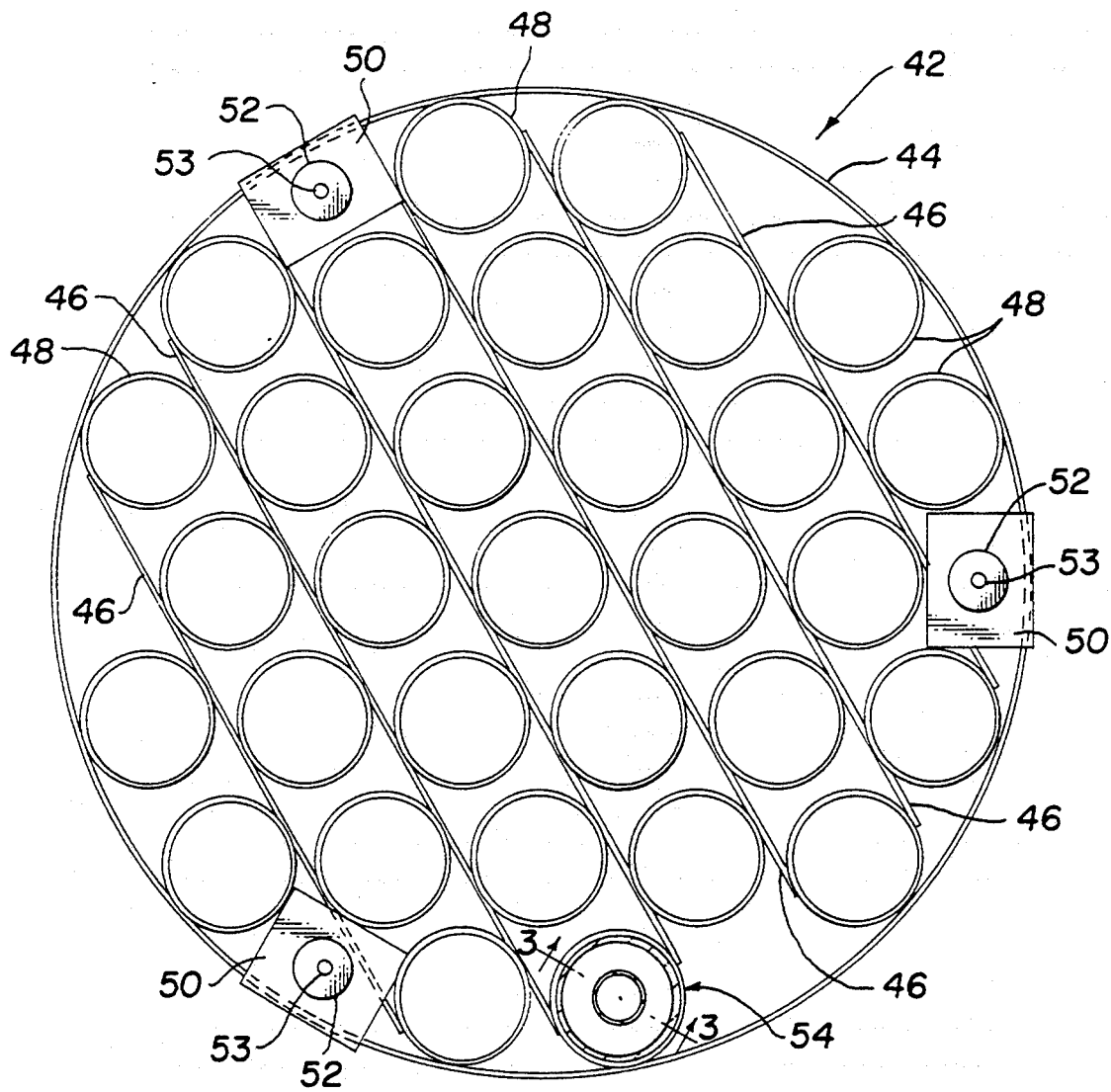
FIG. 2 is a top plan view of the wiper assembly according to a preferred embodiment of the invention.

Referring now to FIG. 2 of the drawings, the wiper assembly 40 includes a wiper retaining platform 42. The platform 42 is formed to define a supporting lattice work. The platform 42 is preferably circular in shape such that it is adapted to fit within the cylindrical side wall 12 of the reactor 10. It is to be understood, however, that the wiper retaining platform 42 could be of any convenient shape that fits within the side walls 12 of the reactor 10.

According to one embodiment of the invention, the platform 42 is formed of metal wires, preferably stainless steel. The platform 42 includes a circumferential wire 44 that defines the outer periphery of the platform 42, a plurality of cross wires 46, and a plurality of circular wires 48. The circumferential wire 44, cross wires 46, and circular wires 48 are welded together as shown in FIG. 2 to form the lattice work of the wiper retaining wire platform 42. Each of the circular wires 46 of the wire platform 42 is positioned in the lattice work to co-axially align with one of the vertically oriented cylindrical reactor tubes 30 positioned in the reactor 10. It is to be understood, however, that the platform 42 could be formed of any suitable structural material, for example, it could be formed of a molded plastic.

Continuing to refer to FIG. 2, a plurality of wiper standoff plates 50 are attached at spaced-apart intervals along the circumferential wire 44 of the wiper retaining platform 42. As will be explained in more detail, the number of wiper standoff plates 50 depends on the size of the wiper retaining platform 42. The wiper standoff plates 50 can be made of any suitable structural material, such as metal or molded plastic. According to the illustrated embodiment of the invention, wiper standoff plates 50 are formed of stainless steel metal plate and preferably welded to the upper side of the wires of the wiper retaining platform 42. Each of the rectangular standoff plates 50 has an upwardly extending standoff block 52 welded on the upper side thereof. Each of the blocks 52 has a threaded tap 53, the purpose of which will be explained in more detail with reference to FIG. 4. In the illustrated embodiment, blocks 52 are cylindrical in shape, but they can be of any convenient configuration.

The wiper assembly 40 includes a reactor tube wiper 54 connected to each of the circular wires 48 of the platform 42. For clarity of the illustration in FIG. 2, only one of the wipers 54 is shown connected to the platform 42.

Turning to FIG. 3 of the drawings, the construction of one of the reactor tube wipers 54 is shown in more detail. Each wiper 54 is preferably integrally formed of a resilient material such as a plastic. Most preferably, the wiper 54 is formed of polytetrafluoroethylene (PTFE), which is commercially available under the trademark "TEFLON". The wiper 54 can be formed using conventional molding techniques that are well known in the art.

As illustrated in the drawing, the wiper 54 has a generally cylindrical wall portion 56 that has a central opening defined by inner wall surface 58. The central opening of the cylindrical wall portion 56 has an axis 60. When positioned over the reactor tube 30, the axis 60 of the opening aligns with the central axis of the reactor tube. The inner diameter of the circular opening defined by inner wall surface 58 is preferably greater than the outer diameter of the reactor tube 30. Thus, there is an annular clearance 62 between the inner wall 58 of the wiper 54 and the outer surface of reactor tube 30. The annular clearance 62 allows the wiper to move freely up and down along the length of reactor tube 30.

The cylindrical wall portion 56 of wiper 54 has an upwardly extending blade portion 64 that is preferably deflected inwardly a few degrees toward the central axis 58. When positioned around the reactor tube 30 as shown in FIG. 3, the blade portion 64 engages the surface of the tube 30. When the wiper 54 is moved upward, the blade portion 64 slides along the outer surface of the reactor tube 30 while wiping or scraping off any fouling that may have accumulated on the reactor tube.

The cylindrical wall portion 56 of wiper 54 has a laterally extending circumferential flange portion 66 and a laterally extending circumferential lip portion 68. The flange portion 66 and lip portion 68 are spaced apart to accommodate the cross section of one of the circular wires 48 of the wiper retaining platform 42. The lip portion 68 extends laterally from the wall portion 56 a distance that is about equal to the cross-section diameter of wire 48. The lip portion 68 also has a deflected cam surface 70. The flange portion 66 and lip portion 68 allow the wiper 54 to be removably retained onto a circular wire 48 of the wiper retaining platform 42. To mount the wiper 54 onto the wire 48, it is positioned above wire 48 and the lip portion 68 pressed through the circle defined by the wire. The wire 48 engages the cam surface 70, which helps deflect the resilient lip portion 68 inward for mounting the wiper 54 onto the wire 48. Once forced through the circle defined by the wire 48, the lip portion resiliently returns to its unstrained position. The wire 48 is captured between the flange 66 and the lip 68. Thus, a wiper 54 is retained onto each of the circular wires 48 of the platform 42.

The wiper assembly 40 also includes a plurality of slide rods that can be removably attached to the platform 42 at the standoff plates 50. As shown in FIG. 4 of the drawing, a slide rod, generally referred to by the reference numeral 72, includes a ball knob 74 and a rod 76. The ball knob 74 is of a size adapted to be grasped by a person's hand. The knob 74 is preferably made of a suitable rigid plastic material that has a threaded tap formed therein. The upper portion of the rod 76 has a correspondingly threaded end to connect to the ball knob 74. The rod 76 is of a suitable length for raising and lowering the platform 42 along the length of a reactor tube 30. The lower portion of the rod 76 has a correspondingly threaded end to connect a standoff block 52 on the platform 42.

The wiper assembly 40 is positioned in an ultraviolet-light reactor such as the one illustrated in FIG. 1. Each wiper 54 of the assembly is supported by a circular wire 48 of platform 42 to coaxially align with one of the plurality of reactor tubes 30 supported in the reactor 10 by the top wall 26. The top wall 26 has a plurality of small apertures that align with the placement of the blocks 52. A slide rod 72 can be positioned through such aligned aperture and the threaded end of the rod 76 screwed into the tap 53 of a standoff block 52.

To periodically clean the reactor tubes 30, one or two persons can grasp one or more of the knobs 74 with their hands to raise and lower wiper assembly 40 one or more times the length of the reactor tubes 30. Alternatively, the slide rods can be connected to a mechanical reciprocator for moving the rods up and down. The wiper platform 42 should be maintained substantially horizontal to the vertically extending reactor tubes 30; if the platform 42 becomes excessively tilted, it might cause the platform 42 to bind such that it cannot move smoothly. It can be desirable to include guide rods (not shown) for maintaining the platform 42 in sliding, perpendicular alignment with the length of the reactor tubes 30.

In the process of raising the wiper assembly 40, the plurality of wipers 54 clean accumulated fouling from the surface of the reactor tubes 30. Wiping the reactor tubes is usually more effective if there is a liquid, such as water, in the reactor. If desired, the removed fouling can be flushed from the system with a purge flow cycle.

When not in use, the wiper assembly 40 can be raised to a stowed position just below the top wall 26 as shown in FIG. 1. The slide rod 72 can be unscrewed from the threaded tap 53 of standoff block 52 and stored out of the way. The slide rod 72 can be replaced by a relatively short retaining bolt that holds the wiper platform 42 in a stowed position adjacent the top wall 26.

FIG. 5 of the drawing shows an alternative embodiment of a wiper assembly, generally referred to by the reference numeral 140. The wiper assembly 140 is similar to the wiper assembly 40 shown in FIG. 2, except that it may or may not have standoff plates 50 for attaching slide rods. As shown in FIG. 5, the wiper assembly 140 is provided with one or more floats 150. Similar to previously described wiper assembly 40, the wiper assembly 140 is positioned within a reactor chamber 24.

The floats 150 can be formed of any suitable material to lower the effective density of the wiper apparatus 140 such that it will float near the water level 38. For example, the floats 150 can be made of substantially hollow or porous plastic bodies in which the hollow space is filled with air.

The particular position of the floats and how they are attached to the wiper assembly 140 is not particularly important. For example, if formed of molded plastic, they can be integrally formed to have plastic clip portions 152 for attaching to the wires of the wiper assembly 140.

In the presently most preferred embodiment, three floats 150 are positioned at equally spaced intervals adjacent the circumferential wire of the wiper assembly 140. The floats 150 are also positioned above the wire frame of the wiper assembly 140 as shown in FIG. 5 so that the wiper assembly 140 is floated in the reactor chamber 24 such that the wipers 54 are positioned beneath the water level 38. This is because wiping the reactor tubes 30 is usually more effective if water is present.

The floats 150 are used to cause the wiper assembly 140 to move with the water level 38 in the reactor chamber 24. Thus, the wiper assembly 40 can be floated such that the wipers 54 are near the water level 38, as shown in FIG. 1. When the reactor chamber 24 is drained, the wiper assembly 40 lowers with the water level 38, and when the reactor chamber 24 is filled, the wiper assembly 40 raises with the rising water level 38. With each lowering or raising of the wiper assembly 40, the wipers 54 clean fouling and scale from the surfaces of the reactor tubes 30. In batch treatment processes, the reactor tubes 30 are cleaned with each batch of water to be treated will the filling and draining of the reactor chamber. Otherwise, the reactor chamber can be periodically drained and filled for the purpose of lowering and raising the floating wiper assembly.

The description and drawings of the specific examples above do not point out what an infringement of this patent would be, but are to provide at least one explanation of how to make and use the invention. Numerous modifications and variations of the preferred embodiments can be made without departing from the scope and spirit of the invention. Thus, the limits of the invention and the bounds of the patent protection are measured by and defined in the following claims.

Having described the invention, what is claimed is:

1. An ultraviolet-light reactor comprising: a bottom wall and side walls defining a reactor chamber; at least one ultraviolet-light reactor tube supported within the reactor chamber; an inlet port and an outlet port for circulating a fluid through the reactor chamber; a wiper having circular opening sufficiently large to accommodate the reactor tube and having a blade circumferential of the opening, the blade being deflected such that when the reactor tube is positioned through the opening, the blade engages the outer surface of the reactor tube; a support platform positioned within the reactor chamber, the platform supporting the wiper in the reactor chamber such that the reactor tube extends through the opening; and at least one float attached to the platform, whereby the platform floats near the surface of water in the reactor chamber to raise with the water level when the reactor chamber is filled and lower when the chamber is drained.

2. An apparatus according to claim 1, wherein the floats are attached to the wiper platform such that the wiper is positioned below the surface of the water in the reactor chamber.

3. An apparatus according to claim 2, wherein the means for moving the wiper platform further comprises at least one rod connected to the platform and extending outside the reactor chamber for mechanically sliding the platform along the length of the reactor tube in the chamber.

4. Apparatus for cleaning accumulated fouling on a reactor tube positioned in a chamber of an ultraviolet-light reactor, the apparatus comprising: a wiper, the wiper having an opening sufficiently large to accommodate the reactor tube, the opening having a peripheral blade deflected such that when the reactor tube is positioned through the opening, the blade engages the surface of the reactor tube; a wiper retaining platform for supporting the wiper; and means for moving the wiper retaining platform in the reactor, said means having at least one float attached to the platform, whereby the wiper platform floats near the surface of water in the reactor chamber to raise with the water level when the reactor chamber is filled and to lower when the chamber is drained, such that when the wiper is moved along the length of the reactor tube, the peripheral blade slides along the outer surface of the reactor tube, thereby wiping off at least some of the fouling on the outer surface of the reactor tube.

5. An apparatus according to claim 4, wherein the floats are attached to the wiper platform such that when the platform is floated in water within the reactor, the wiper is positioned below the surface of the water in the reactor chamber.

6. An apparatus according to claim 4, wherein the means for moving the wiper platform further comprises at least one rod connected to the platform and extending outside the reactor chamber for mechanically sliding the platform along the length of the reactor tube in the reactor chamber.

7. An ultraviolet-light reactor comprising: a bottom wall and side walls defining a reactor chamber; a plurality of ultraviolet-light reactor tubes, the reactor tubes supported in the chamber With the axes of the tubes in parallel alignment within the reactor chamber; an inlet port and an outlet port for circulating a fluid through the reactor chamber; a plurality of wipers, each wiper having a circular opening sufficiently large to accommodate the circumference of one of the reactor tubes in the reactor chamber, each wiper having a blade circumferential of the opening, the blade being deflected such that when one of the reactor tubes is positioned through the opening, the blade engages the outer surface of the reactor tube; a support platform positioned within the reactor chamber, wherein the platform has a plurality of platform openings positioned in the platform so that the reactor tubes can extend therethrough, wherein each of the wipers has a generally cylindrical wall portion, a laterally extending flange portion, a laterally extending lip portion that is spaced apart from the flange portion, whereby when the wiper is positioned in one of the openings of the platform, the flange portion and the lip portion capture the platform therebetween to retain the wiper on the platform; each of the wipers is attached to the platform at one of the platform openings so that the reactor tubes can also extend through the wipers supported by the platform; the platform supporting the plurality of wipers in the reactor chamber such that each of the reactor tubes is co-axially aligned with the opening of one of the wipers and extends through the opening; and at least one rod for mechanically reciprocating the platform along the length of the reactor tube in the chamber, whereby, the blade slides along the outer surface of the reactor tube to wipe off at least some of the fouling that may have accumulated on the outer surface of the reactor tube.

* * * * *